(12) United States Patent
Hijlkema et al.

(10) Patent No.: US 7,010,850 B2
(45) Date of Patent: Mar. 14, 2006

(54) THERMAL REGULATION OF A COATED WORK-PIECE DURING THE RECONFIGURATION OF THE COATED WORK-PIECE

(75) Inventors: Luuk Hijlkema, Moycullen (IE); Michael Austin, Tuam (IE); Jan Weber, Taum (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 129 days.

(21) Appl. No.: 10/812,031

(22) Filed: Mar. 30, 2004

(65) Prior Publication Data

US 2004/0177805 A1    Sep. 16, 2004

Related U.S. Application Data

(63) Continuation of application No. 09/819,638, filed on Mar. 29, 2001, now Pat. No. 6,739,033.

(51) Int. Cl.
*B23P 11/00*    (2006.01)

(52) U.S. Cl. ............................. 29/702; 29/703; 29/252; 29/407.05; 29/447; 118/101

(58) Field of Classification Search ............ 29/407.05, 29/447, 458, 508, 516, 252, 272, 283.5, 702, 29/703, 722; 606/1, 108; 623/1.12, 1.19, 623/1.2, 1.46; 427/2.1; 118/101
See application file for complete search history.

(56) References Cited

U.S. PATENT DOCUMENTS

| | | | |
|---|---|---|---|
| 3,661,655 A | 5/1972 | Hrusovsky |
| 5,183,085 A | 2/1993 | Timmermans |
| 5,288,356 A | 2/1994 | Benefiel |
| 5,353,623 A | 10/1994 | Bobenhausen |
| 5,485,667 A | 1/1996 | Kleshinski |
| 5,546,646 A | 8/1996 | Williams et al. |
| 5,630,830 A | 5/1997 | Verbeek |
| 5,725,519 A | 3/1998 | Penner et al. |

(Continued)

FOREIGN PATENT DOCUMENTS

DE    195 32 2888    3/1997

(Continued)

OTHER PUBLICATIONS

European International Search Report, Aug. 23, 2002.

(Continued)

*Primary Examiner*—David P. Bryant
*Assistant Examiner*—Jermie E. Cozart
(74) *Attorney, Agent, or Firm*—Kenyon & Kenyon

(57) ABSTRACT

Apparatus for configuring an externally coated workpiece are provided. In one example, the apparatus includes a tubular reconfiguration chamber having a plurality of slidably mounted outer walls, the outer walls slidably mounted along individual radial lines emanating from and orthogonal to the central longitudinal axis of the tubular reconfiguration chamber; and a device for adjusting and maintaining the temperature of the external coating of a work-piece located within the tubular reconfiguration chamber. In another example the apparatus includes a reconfiguration chamber; a nozzle in fluid communication with the reconfiguration chamber, a regulator in fluid communication with the nozzle, the regulator adapted to regulate the flow of a thermal transfer fluid exiting the nozzle, and a controller in communication with the regulator, the controller adapted to send control signals to the regulator to maintain the surface temperature of the external coating of the reconfigurable work-piece within a predetermined temperature range, the predetermined temperature range associated with a predetermined minimum hardness of the external coating of the reconfigurable work-piece.

10 Claims, 5 Drawing Sheets

U.S. PATENT DOCUMENTS

| | | |
|---|---|---|
| 5,766,158 A | 6/1998 | Opolski |
| 5,860,966 A | 1/1999 | Tower |
| 5,893,867 A | 4/1999 | Bagaoisan et al. |
| 5,893,868 A | 4/1999 | Hanson et al. |
| 5,899,935 A | 5/1999 | Ding |
| 5,911,452 A | 6/1999 | Yan |
| 5,931,851 A | 8/1999 | Morales |
| 5,951,540 A | 9/1999 | Verbeek |
| 5,992,000 A | 11/1999 | Humphrey et al. |
| 6,009,614 A | 1/2000 | Morales |
| 6,024,737 A | 2/2000 | Morales |
| 6,063,092 A | 5/2000 | Shin |
| 6,065,197 A | 5/2000 | Iseki et al. |
| 6,245,076 B1 | 6/2001 | Yan |
| 6,249,952 B1 | 6/2001 | Ding |
| 6,292,990 B1 | 9/2001 | Iseki et al. |

FOREIGN PATENT DOCUMENTS

| | | | |
|---|---|---|---|
| EP | 0301168 | * | 2/1989 |
| WO | WO 97/20593 | | 6/1997 |
| WO | WO 01/91918 A1 | | 12/2001 |

OTHER PUBLICATIONS

Patent Abstracts of Japan, vol. 2000, No. 09, Oct. 13, 2000, Publication No. 2000161344, Manufacture of Tube-Covered Roller, Tube-Covered Roller, and Hating Fixing Device with Tube-Covered Roller, U.S. Appl. No. 10/355,412.

* cited by examiner

THERMAL REGULATION OF A COATED WORK-PIECE DURING THE RECONFIGURATION OF THE COATED WORK-PIECE

CROSS-REFERENCE TO RELATED APPLICATIONS

This application is a Continuation of application Ser. No. 09/819,638, filed Mar. 29, 2001 now U.S. Pat. No. 6,739,033, which is included herein in its entirety by reference.

TECHNICAL BACKGROUND

The present invention regards protecting a coated work-piece during its manufacture or reconfiguration. More specifically the present invention regards reducing the probability of damaging the coating of a work-piece during the work-piece's manufacture by managing or regulating the temperature of the coating.

BACKGROUND OF THE INVENTION

Articles of manufacture are regularly coated for numerous and varying reasons. For example, they may be coated to protect them from the intrusive handling they may be subjected to during their manufacture or to protect them from the environmental effects they may endure after they are manufactured. In either of these, as well as in others, damage to the coating of a work-piece, resulting from the handling or reconfiguration of the work-piece, is an unwanted result.

When the coating of a work-piece becomes scratched or otherwise damaged during the work-piece's manufacture, the scratches can promote the deterioration of the work-piece by exposing the work-piece's surface to its surroundings. Should the work-piece, upon its completion, be employed in a corrosive environment, the exposed surface of the finished product would be more vulnerable to corrosion than if its coating were completely intact. Moreover, the scratches and inconsistencies in the coating of the work-piece may also reduce the effectiveness of the finished product. For example, should the coating be used to uniformly deliver some type of releasable substance, inconsistencies in the surface of the coating can foster uneven and inconsistent delivery of the releasable substance to the deployed product's final surroundings.

An expandable coated stent is one specific example of the coated work-pieces described above. Expandable stents are tube-like medical devices designed to support the inner walls of a vessel within the body of a patient. These stents are typically positioned within a targeted lumen of the body and then expanded to provide internal support for the lumen. These stents may be self-expanding or, alternatively, may require external forces to expand them. In either case they are typically deployed through the use of a catheter of some kind. These catheters typically carry the stent at their distal ends. In use, a practitioner will position the catheter's distal end near the target area of the lumen. Once properly positioned the stent will be deployed by the practitioner such that it comes to rest near or in direct contact with the inner walls of the lumen. There, the stent will remain to provide support for the lumen.

Due to the interaction of the stent with the inner walls of the lumen, stents have been coated to enhance their effectiveness. These coatings may, among other things, be designed to facilitate the acceptance of the stent into its applied surroundings or to enable the delivery of therapeutic to the lumen and its surroundings. Thus, when the coating is haphazardly applied or has somehow been removed during the stent's manufacture, both the stent's longevity and its effectiveness can be reduced.

The coatings on the stent may be applied at various times during its life cycle including its manufacture, its placement onto the distal end of the delivery catheter, and contemporaneous with the medical procedure. At each of these times the coating may be at risk of being scratched, damaged or otherwise removed from the surface of the stent. For example, during their manufacture, stents are often crimped onto the distal end of a delivery catheter. This crimping process requires the exertion of significant forces against the coating of the stent to facilitate a reduction in the stent's circumference to secure it to the catheter. During this crimping, the mechanical arms of a crimper may come in contact with the coating of the stent as they reduce the diameter of the stent. This compressive contact can scratch, indent, wipe-off or otherwise breach the integrity of the coating—an undesirable result.

SUMMARY OF THE INVENTION

Apparatus for configuring an externally coated workpiece are provided. In one example, the apparatus includes a tubular reconfiguration chamber having a plurality of slidably mounted outer walls, the outer walls slidably mounted along individual radial lines emanating from and orthogonal to the central longitudinal axis of the tubular reconfiguration chamber; and a means for adjusting and maintaining the temperature of the external coating of a work-piece located within the tubular reconfiguration chamber.

In another example the apparatus includes a reconfiguration chamber; a nozzle in fluid communication with the reconfiguration chamber, a regulator in fluid communication with the nozzle, the regulator adapted to regulate the flow of a thermal transfer fluid exiting the nozzle, and a controller in communication with the regulator, the controller adapted to send control signals to the regulator to maintain the surface temperature of the external coating of the reconfigurable work-piece within a predetermined temperature range, the predetermined temperature range associated with a predetermined minimum hardness of the external coating of the reconfigurable work-piece.

DETAILED DESCRIPTION

In one embodiment of the present invention the hardness or resilience of the coating of a work-piece is temporarily increased by adjusting its preexisting temperature to be closer to its glass transition temperature. Then, while the coating is in this temporarily hardened or more resilient state, the force required to reconfigure the work-piece is applied against the coating. By temporarily increasing the hardness of the coating through its change in temperature, the coating is better able to withstand the forces and pressures exerted upon it during the reconfiguration of the work-piece. Thus, the coating is more likely to remain intact both during the remainder of the manufacturing of the work-piece and after the work-piece has been completely manufactured and is employed for its intended purpose.

Figure 1:
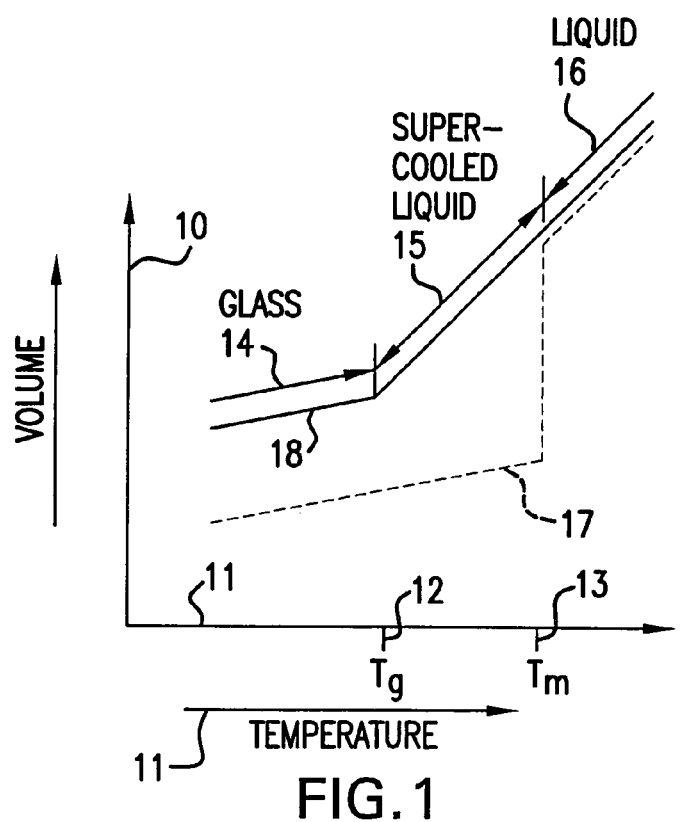
FIG. 1 is a graph of volume versus temperature for an exemplary polymer coating.

FIG. 1 is a graph of volume versus temperature for a polymer that may be used as a coating in accord with one embodiment of the present invention. The temperature of the polymer is plotted along the x-axis 11 while its corresponding volume is plotted along the y-axis 10. The glass transition temperature $(T_g)$ 12 as well as the melting temperature $(T_m)$ 13 are specifically labeled on the x-axis 11 of the graph. Also labeled in the graph is the line 18 representing the specific volume for a given temperature of this exemplary polymer. This line 18 has three phase ranges identified on it, the glass phase 14, the super-cooled liquid phase 15, and the liquid phase 16. The crystalline property delineation line 17 for this exemplary polymer is also evident in FIG. 1.

The exemplary polymer graphed in FIG. 1 is a typical polymer. It is comprised of chains or strings of molecules that are interwoven and able to move in and around one another. As the polymer cools the chains loose their ability to freely flow around and among one another, and, thus, the polymer becomes stiffer and decreases in volume.

When the polymer temperature is within the liquid range 16 the chains of molecules comprising the polymer may move freely amongst one another and, consequently, the polymer behaves much like a liquid. As the temperature decreases, the thermal agitation among the molecules lessens and the volume of the liquid shrinks. This decrease in volume continues below the melting point $(T_m)$ 13 of the polymer and into its super-cooled liquid range. Below the melting point $(T_m)$ 13, the chains of molecules may still flow around and among themselves but they do so at a lower rate than in the liquid phase. It is here, in this super-cooled liquid range, that the hardness and resiliency of the polymer will increase as its temperature approaches the glass transition temperature $(T_g)$ 12. When the temperature of the polymer reaches the glass transition temperature $(T_g)$ 12 the polymer enters the glass phase 14. Here, the polymer becomes more brittle than in the super-cooled liquid phase as the molecules can no longer continually rearrange themselves. Moreover, as is evident in the graph of FIG. 1, the rate of volume change in relation to temperature changes at this point as it is one constant above the glass transition temperature $(T_g)$ 12 and a different constant below the glass transition temperature $(T_g)$ 12.

Figure 2:
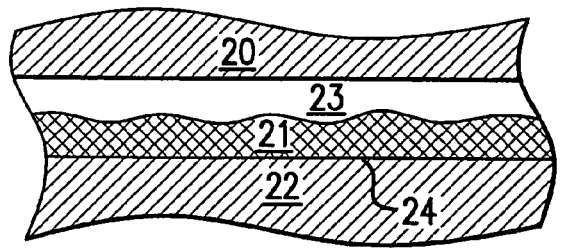
FIG. 2 is an enlarged partial side cross-sectional view of a reconfiguration chamber and a reconfigurable coated work-piece prior to the reconfiguration of the coated work-piece in accord with an embodiment of the present invention.

FIG. 2 provides an enlarged partial cross-section of a slidable outer wall 20 of a reconfiguration chamber positioned near a reconfigurable work-piece 22, prior to a work stroke, in accord with one embodiment of the present invention. In this embodiment, prior to the beginning of a work stroke, the slidable outer wall is not in contact with the coating 21 or the reconfigurable work-piece 22 as is evident by the existence of void 23.

Figure 3:
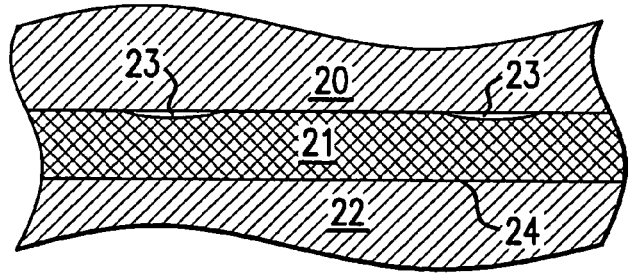
FIG. 3 is the view of FIG. 2 shown during the reconfiguration of the coated work-piece in accord with an embodiment of the present invention.

FIG. 3 provides an enlarged cross-section of the slidable outer wall 20 and the reconfigurable work-piece 22 of FIG. 2 during a work stroke. As can be seen, the slidable outer wall 20 is in direct contact with the coating 21 of the reconfigurable work-piece 22. As is also evident, most but not all of the void 23 is filled during the work stroke as some small areas of void 23 remain when the slidable outer wall 20 comes in contact with the coating.

In order to increase the resiliency and hardness of the coating and to reduce the potential damage to it from the direct contact with the slidable outer wall 20, the coating may be cooled to be within its super-cooled liquid range. By lowering the temperature of the coating 21, closer to the glass transition temperature of the coating, the coating 21 can be sufficiently hardened to protect it from the forces generated by its direct contact with the slidable outer wall 20. Due to this temporal hardening, the coating 21 may remain substantially intact on the work-piece and may be able to continue to protect the work-piece 22 during the remaining steps of its manufacture and, afterwards, as the work-piece is deployed for its intended use.

The slidable outer wall 20 provided in FIGS. 2–3 may be any one of innumerable pinching, moving, or force exerting components of a manufacturing machine or process. Likewise, the reconfigurable work-piece may be any one of innumerable work-pieces or products of manufacture currently manufactured in modem manufacturing systems. In addition, the coating 21 may be one of numerous commercial or industrial coatings including various ceramics, polymers, and waxes. These polymers could include SIBS polymers (styrene-isobutylene-styrene) and any other suitable polymer.

Figure 4:
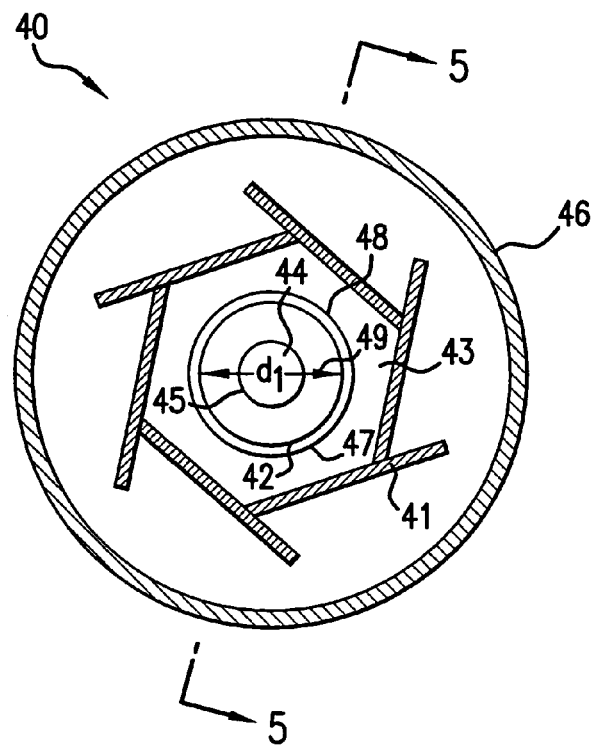
FIG. 4 is a cross-sectional view of a reconfiguration chamber shown prior to the execution of a work stroke in accord with an alternative embodiment of the present invention.

FIG. 4 is a cross-sectional view of a reconfiguration chamber 40 as may be used to crimp or crease a stent 42 onto the distal end of a balloon catheter 44 in accordance with an alternative embodiment of the present invention. As can be seen in FIG. 4, the reconfiguration chamber 40 has slidable outer walls 41 that are in physical communication with one another and define a hexagonal-like adjustable aperture. Resident within this aperture is the distal end of a balloon catheter 44 having an exterior wall 45. A stent 42, encircling the distal end of the balloon catheter 44 and having a coating 47 with an exterior surface of the coating 48, is also pictured in FIG. 4. As can also be seen in this embodiment, the exterior surface of the coating 48 has a void 43 between it and the interior faces of the slidable outer walls 41. This void 43 may exist both before and after the completion of a work stroke of the slidable outer walls 41. The initial diameter of the stent 42, prior to the completion of a work stroke, is indicated with the character $d_1$ and the numeral 49.

In this embodiment, the slidable outer walls 41 of the reconfiguration chamber 40 are activated to crimp the stent 42 onto the balloon catheter 44. When activated, the slidable outer walls 41 slide towards one another and, thus, reduce the size of the aperture defined by them. As the aperture's diameter reaches the size of the exterior surface 48 of the coating 47, pressure is begun to be exerted on the coating 47 of the stent 42 and the stent begins to be reconfigured. As the diameter of the aperture is further reduced so too is the cross-sectional diameter of the stent 42. In order to retard damage to the coating 47 that contacts the slidable outer walls 41, the temperature of the coating 47 has been adjusted either before placing the stent 42 into the reconfiguration chamber 40 or while the stent 42 is located within the reconfiguration chamber 40.

In this embodiment the temperature of the coating 47 is adjusted after the stent has been placed within the reconfiguration chamber 40. Here, a thermally conductive fluid may be flushed through the void 43 and in contact with the coating 47 to adjust the coating's temperature. Dependant upon the ambient temperature, the coating's preexisting temperature, and the glass transition temperature of the coating, the temperature of the existing surface of the coating 47 may be either heated or cooled. In this embodiment the temperature of the coating is reduced through the introduction of cooled ultra-dry air into the void 43 until the desired resultant temperature of the coating 47 is achieved. Other cooling mediums may also be used including both compressible and non-compressible fluids. The desired resultant temperature may depend upon the glass transition temperature of the coating, the structural rigidity of the stent, the properties of the balloon catheter, and the anticipated future handling of the stent. The desired temperature or temperature range may be a percentage of the $T_g$ or it may be a specific range of quantified values. In this embodiment, the desired temperature range is approximately 20° Celsius above the glass transition temperature of the coating.

Figure 6:
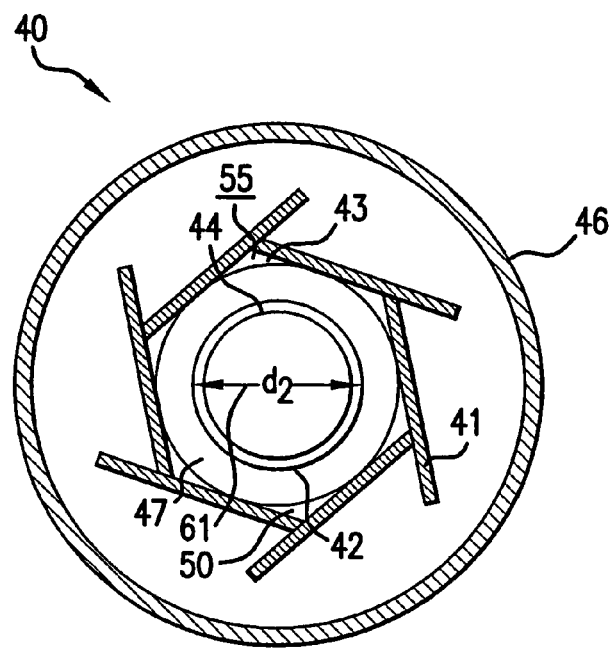
FIG. 6 is another cross-sectional view of the reconfiguration chamber of FIG. 4 shown after a work stroke has been completed in accord with an alternative embodiment of the present invention.

In this embodiment, once the temperature of the coating has been adjusted to be within the desired temperature range, the slidable outer walls 41 may complete a work stroke by sliding inwardly and, consequently, reconfiguring the stent 42 from a first position having a diameter $d_1$ to a second position having a diameter $d_2$ (illustrated in FIG. 6).

An insulating tube 46 is positioned around the slidable outer walls 41 and is clearly evident in FIG. 4. This insulating tube 46 provides additional thermal buffering between the potentially extreme temperatures generated within the reconfiguration chamber and its surroundings. The insulating tube 46 may be made from an insulating ceramic or any other suitable insulating material. The slidable outer walls 41 may also be designed to provide buffering between the extreme temperatures generated within the reconfiguration chamber and the surroundings. For example the slidable outer walls 41 may be made from materials such as Dupont™ Delrin™ (acetal homopolymer and copolymer) and Zirconium oxide ceramic which has been partially stabilized with Yttria to provide supplementary thermal buffering between the work-piece and the surrounding area.

Figure 5:
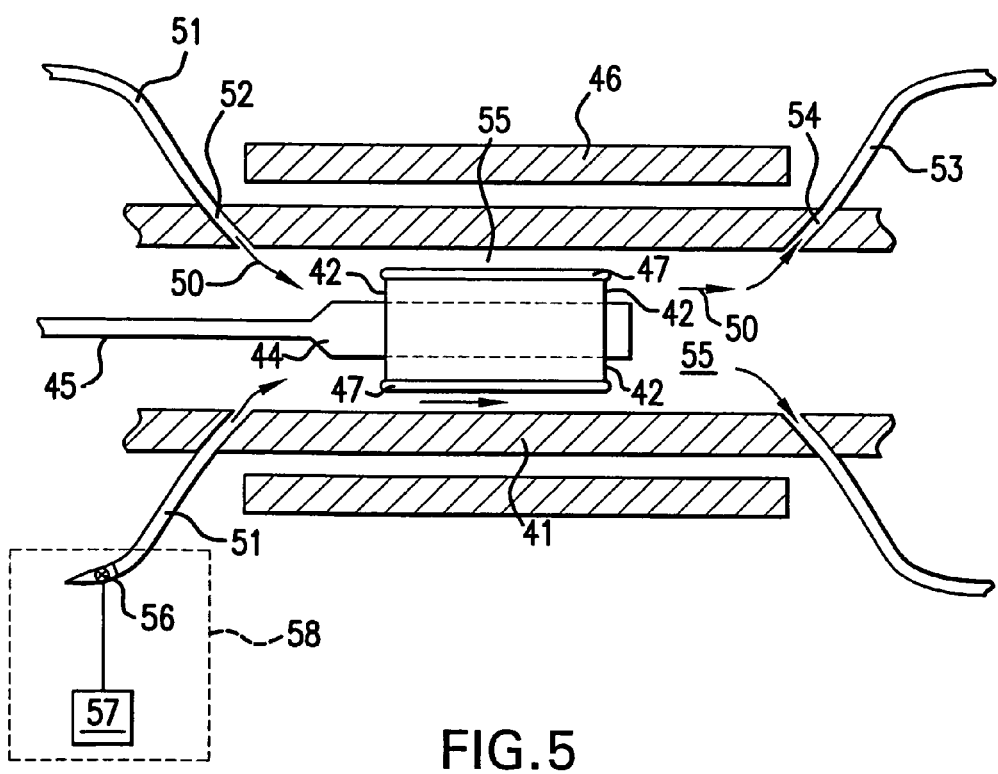
FIG. 5 is a sectional view taken along line 5—5 of FIG. 4.

FIG. 5 is a side cross-sectional view taken along line 5—5 of the reconfiguration chamber 40 of FIG. 4. Various features of the reconfiguration tube 40 are evident in this illustration including the entrance tube 51, the exit tube 53, nozzles 52 and 54, insulating tube 46, coating 47, thermal transfer fluid flow arrows 50, thermal transfer fluid 55, stent 42, slidable outer walls 41, balloon catheter exterior surface 45, balloon catheter 44, regulator 56, and controller 57.

After the distal end of the catheter 44 has been placed within the reconfiguration chamber 40, in order to adjust the temperature of the coating 47, thermal transfer fluid 53 may be delivered through tube 51 and nozzle 52 into direct contact with the coating 47. Then, after passing over the coated stent, the fluid 50 may be recaptured through nozzles 54 and exit tubes 53 where it can be stored or recycled back into the process. The thermal transfer fluid 55 may be introduced and circulated both prior to and during the reconfiguration of the stent 42, although it is preferable that the flow of the thermal transfer fluid 55 be halted once the slidable outer walls 41 have begun to move. The thermal transfer fluid may be any one of numerous suitable fluids, including liquid nitrogen, water, liquid helium, dry air, nitrogen, helium, or any other suitable compressible and non-compressible fluids.

After the crimping has occurred the slidable outer wall 41 may open and the thermal transfer fluid 55 may cease its flow through the chamber. The balloon catheter 44 may then be removed from the reconfiguration chamber 40 and its temperature permitted to return to the ambient temperature. Alternatively, the distal end of the catheter 44, carrying the now crimped stent 42, may be subjected to other manufacturing steps that may also benefit from the coating's temporally increased hardness.

In this embodiment the regulator 56 and controller 57 act together as a means for adjusting and maintaining the temperature of the coating 58 although other configurations for this means are plausible. These components work together to adjust and maintain the temperature of the coating 47. The amount of fluid flowing through the entrance nozzles 52 into the reconfiguration chamber may be monitored by the controller 57. When the requisite flow is detected no action may be required. However, should the controller 57 determine that the rate of fluid flow should be adjusted, in order to adjust or maintain the temperature of the coating 47, it may, as required, send a signal that opens or closes the regulator 56.

This means for adjusting and maintaining the temperature 58 can take numerous other configurations. For example, while it is illustrated as being comprised of regulators and controllers regulating the flow of fluid into the reconfiguration chamber, this means could, instead, comprise manually adjustable valves that are adjusted by an operator monitoring the temperature of the coating. Alternatively, this means could also be electrical coils or hollow thermal conduction tubes carrying a thermal conductive fluid such as liquid nitrogen. The coils in either case may be placed within the slidable outer walls 41 and may be used to provide the thermal adjustment of the coating of the stent via the regulation of the fluid or electrical current flowing through them.

FIG. 6 provides an enlarged cross-sectional view of the reconfiguration chamber during a work stroke. As can be seen in FIG. 6 the slidable outer walls 41, containing residual transfer fluid 55 in the voids 43, have closed in on themselves and have reconfigured the stent 42 into a second position such that the diameter $d_2$ of the stent 42 is smaller than the diameter $d_1$ of the stent 42 in FIG. 4. Because the temperature of the coating was brought closer to its glass transition temperature, the coating has substantially retained its shape, has not been substantially damaged, and has adequately transferred the forces generated from the slidable outer walls to the stent 42.

Figure 7:
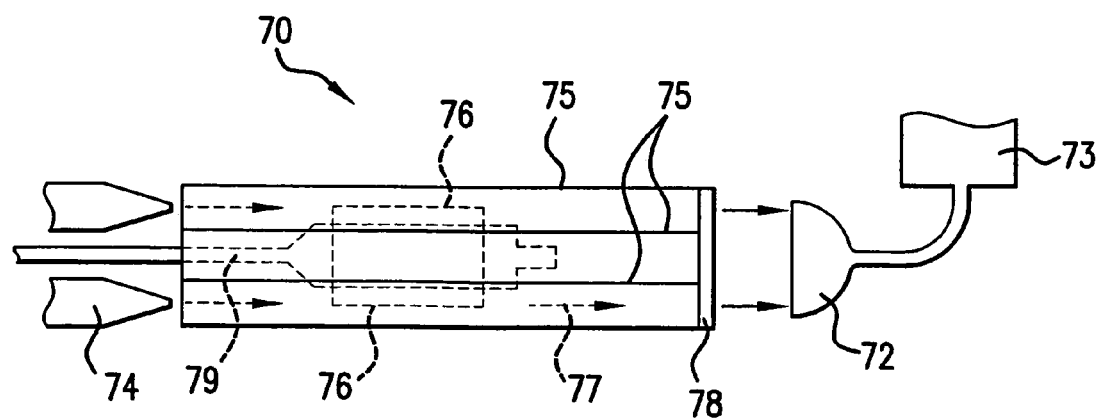
FIG. 7 is a side view of a reconfiguration chamber in accord with another alternative embodiment of the present invention.

FIG. 7 shows a side view of a reconfiguration chamber in accord with another alternative embodiment of the present invention. In FIG. 7, nozzle 74, catheter 79, stent 76, flow arrow 77, thermocouple 78, slidable outer walls 75, uptake 72, and thermal transfer fluid storage chamber 73 are all clearly evident. In this embodiment, after placing the distal end of the catheter into the reconfiguration chamber, the nozzle 74 may be used to inject thermal transfer fluid into the reconfiguration chamber 70 in order to adjust the temperature of the coating resident on stent 76. In this embodiment, the thermocouple 78 may be used to monitor the temperature of the thermal transfer fluid leaving the reconfiguration chamber such that the stent resident within the reconfiguration chamber 70 may be adjusted to a desired target temperature. In this embodiment, the uptake 72 may be positioned near the exit of the reconfiguration chamber 70 and may be used to capture thermal transfer fluid leaving the reconfiguration chamber in a thermal transfer fluid storage chamber 73 for subsequent disposal or reuse.

Although not illustrated in this figure, the thermocouple 78 may be in communication with a controller to act in conjunction with it as a means for adjusting and maintaining the temperature of the coating.

Figure 8:
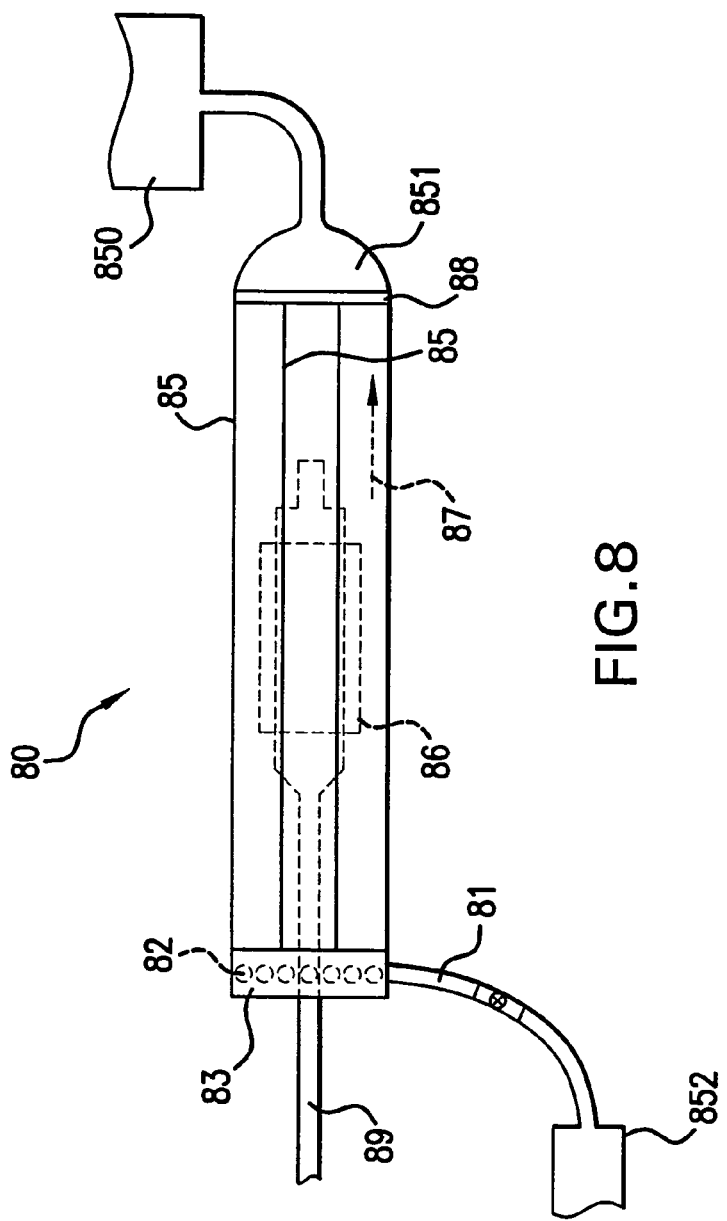
FIG. 8 is a side view of a reconfiguration chamber in accord with another alternative embodiment of the present invention.

FIG. 8 is a side view of an alternative reconfiguration chamber in accord with another alternative embodiment of the present invention. Illustrated in FIG. 8 are thermal transfer fluid storage chambers 850 and 852, entrance tube 81, couple ring 83, catheter 89, nozzles 82, stent or work-piece 86, fluid flow arrows 87, slidable outer walls 85, thermocouple 88, and uptake 851. While similar to the embodiment in FIG. 7, the embodiment of FIG. 8 utilizes a couple ring 83 in fluid communication with numerous nozzles 82 that travel through the slidable outer walls 85. These nozzles direct the thermal transfer fluid into the reconfiguration chamber and may be designed to increase or decrease the velocity of the fluid's flow in relation to its velocity in the tube 81. By increasing or decreasing the flow of the fluid, the thermal transfer rate between the fluid and the coating can be concomitantly increased or decreased.

Figure 9:
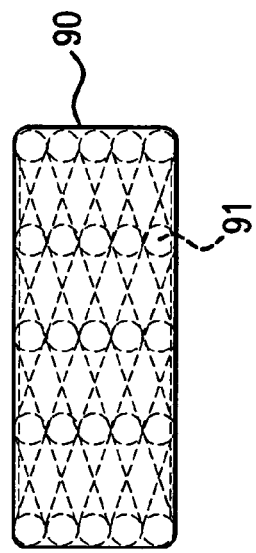
FIG. 9 is a side view of a self-expanding stent within a sheath as manufactured by a method in accord with another alternative embodiment of the present invention.

While several of the above embodiments describe a balloon expandable stent, self-expanding stents may also be crimped in accord with the processes described above. These self-expanding stents, rather than requiring the forces generated by the balloon catheter to expand them, are capable of expanding under their own power once they have been deployed. In FIG. 9, as can be seen, the stent, previously crimped by the processes described above to fit inside the sheath 90, may be stored within the sheath 90, where it will remain until it is deployed at a target site of the body. Upon being deployed, the sheath 90 may be removed thereby allowing the stent 91 to expand under its own forces.

As described above and as shown in FIGS. 10 and 11, the slidable outer walls may contain conduits or lines for adjusting the temperature of the coating.

Figure 10:
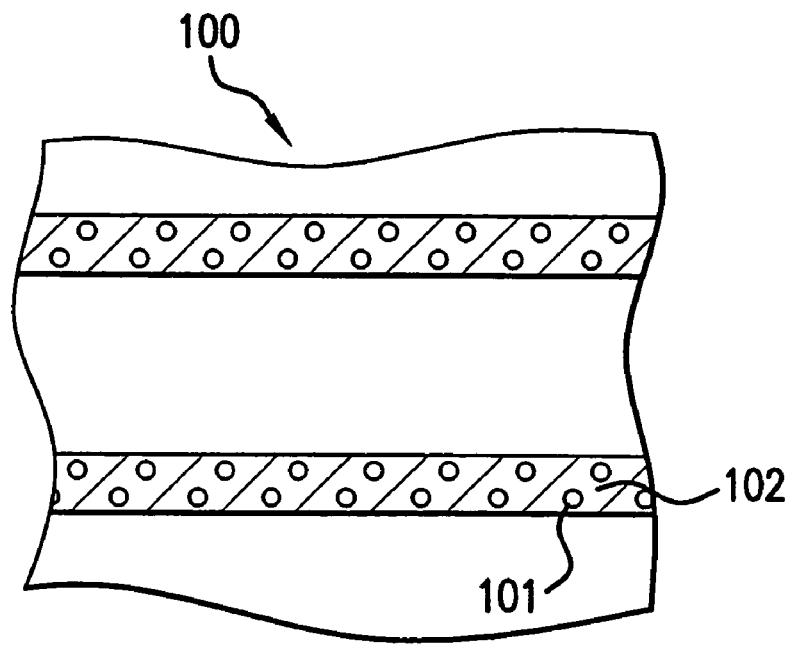
FIG. 10 is an enlarged side cross-sectional view of a reconfiguration chamber in accord with another alternative embodiment of the present invention.

In FIG. 10, which is a side sectional view of reconfiguration chamber 100, the slidable outer walls 102 are shown with fluid conduits 101. These fluid conduits may be looped and travel throughout the individual slidable outer walls and may contain a thermal transfer fluid to adjust the temperature of the slidable outer wall 102. This fluid may be cooled air and may be pumped through the conduits by a pumping system (not shown).

Figure 11:
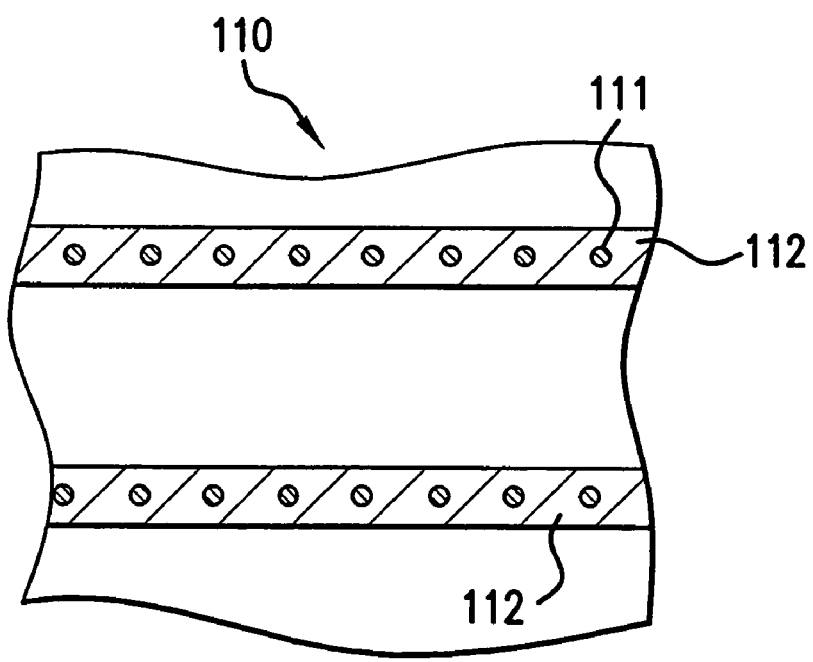
FIG. 11 is an enlarged side cross-sectional view of a reconfiguration chamber in accord with another alternative embodiment of the present invention.

FIG. 11 is a side sectional view of a reconfiguration chamber 110. Rather than providing for a fluid conduit as in FIG. 10, the slidable outer walls 112 in FIG. 11 contain electrical lines 111. These electrical lines, like the conduits described above, may be used to raise the temperature of the coating rather than lower it to reach the desired resiliency or, alternatively, may be used to thaw the coating after the stent has been reconfigured and prior to its ejection from the reconfiguration chamber 110.

These conduits or lines may be used in place of the thermal fluid transfer methods described above or in addition to the thermal fluid transfer methods described above. In other words, the conduits or lines placed into the walls 102 and 112 may be the sole source of adjusting the temperature of the coating or they may be a supplement to thermal transfer fluid being pumped over the coating. These conduits and lines may also be classified as a means for adjusting and maintaining the temperature of the coating.

Thermal conditioning of a coated work-piece during the reconfiguration of the work-piece is provided. While various embodiments have been conveyed, it will be evident to one of skill in the art that other embodiments, also within the spirit and scope of the present invention, are plausible.

What is claimed is:

1. An apparatus for reconfiguring from a first configuration to a second configuration an externally coated work-piece comprising:
    a tubular reconfiguration chamber having a plurality of slidably mounted outer walls, the outer walls slidably mounted along individual radial lines emanating from and orthogonal to the central longitudinal axis of the tubular reconfiguration chamber; and
    a means for adjusting and maintaining the temperature of the external coating of a work-piece located within the tubular reconfiguration chamber.

2. The apparatus of claim 1 wherein the means for adjusting and maintaining the temperature includes a fluid ejection nozzle in fluid communication with the tubular reconfiguration chamber.

3. The apparatus of claim 1 wherein the means for adjusting and maintaining the temperature is adapted to lower the temperature of the external coating to be within the coating's super-cooled liquid temperature range.

4. The apparatus of claim 1 wherein the means for adjusting and maintaining the temperature is adapted to raise the temperature of the external coating from its preexisting temperature to be within the coating's super-cooled liquid temperature range.

5. The apparatus of claim 1 wherein the tubular reconfiguration chamber has a polygonal cross-section.

6. An apparatus for reconfiguring an externally coated reconfigurable work-piece comprising:
    a reconfiguration chamber;
    a nozzle in fluid communication with the reconfiguration chamber;
    a regulator in fluid communication with the nozzle, the regulator adapted to regulate the flow of a thermal transfer fluid exiting the nozzle; and
    a controller in communication with the regulator, the controller adapted to send control signals to the regulator to maintain the surface temperature of the external coating of the reconfigurable work-piece within a predetermined temperature range, the predetermined temperature range associated with a predetermined minimum hardness of the external coating of the reconfigurable work-piece.

7. The apparatus of claim 6 wherein the controller is further adapted to send control signals to the regulator to modify the surface temperature of the external coating of the reconfigurable work-piece to be at least 20 degrees Celsius closer to the external coating's glass transition temperature.

8. The apparatus of claim 6 wherein the controller is further adapted to send control signals to the regulator to modify the surface temperature of the external coating of the reconfigurable work-piece to be at least 10 degrees Celsius closer to the external coating's glass transition temperature.

9. The apparatus of claim 6 wherein the reconfiguration chamber has a polygonal cross-section.

10. The apparatus of claim 6 wherein the nozzle is incorporated into a wall of the reconfiguration chamber and wherein the nozzle is in fluid communication with a thermal transfer fluid storage chamber.

* * * * *

UNITED STATES PATENT AND TRADEMARK OFFICE
CERTIFICATE OF CORRECTION

| | | |
|---|---|---|
| PATENT NO. | : 7,010,850 B2 | Page 1 of 1 |
| APPLICATION NO. | : 10/812031 | |
| DATED | : March 14, 2006 | |
| INVENTOR(S) | : Hijlkema et al. | |

It is certified that error appears in the above-identified patent and that said Letters Patent is hereby corrected as shown below:

On the title, under OTHER PUBLICATIONS, the reference:

Patent Abstracts of Japan, vol. 2000, No.09, Oct. 13, 2000, Publication No. 2000161344, Manufacture of Tube Covered Roller, Tube-Covered Roller, and Hating Fixing Device with Tube-Covered Roller, U.S. Appln. No. 10/355,412.

should be listed under FOREIGN PATENT DOCUMENTS and should read:

JP  JP 2000161344  6/2000

Column 3, line 49, "loose" should read --lose--.

Signed and Sealed this

Twentieth Day of May, 2008

JON W. DUDAS
*Director of the United States Patent and Trademark Office*